United States Patent [19]
Humes

[11] Patent Number: 6,150,164
[45] Date of Patent: *Nov. 21, 2000

[54] METHODS AND COMPOSITIONS OF A BIOARTIFICIAL KIDNEY SUITABLE FOR USE IN VIVO OR EX VIVO

[75] Inventor: H. David Humes, Ann Arbor, Mich.

[73] Assignee: The Regents of the University of Michigan, Ann Arbor, Mich.

[ * ] Notice: This patent is subject to a terminal disclaimer.

[21] Appl. No.: 08/941,228

[22] Filed: Sep. 30, 1997

Related U.S. Application Data

[60] Provisional application No. 60/027,495, Sep. 30, 1996.
[51] Int. Cl.⁷ .............................. C12N 5/00; C12N 5/02; C12N 5/06; C12N 5/08
[52] U.S. Cl. .................... 435/400; 435/325; 435/347; 435/369; 435/371; 435/373; 435/395
[58] Field of Search ............... 435/289.1, 297.1, 435/297.2, 325, 363, 366, 369, 371, 372, 373, 395, 401, 400

[56] References Cited

U.S. PATENT DOCUMENTS

| | | | |
|---|---|---|---|
| 5,429,938 | 7/1995 | Humes ................................. | 435/240.2 |
| 5,516,680 | 5/1996 | Naughton et al. ................ | 435/240.243 |
| 5,549,674 | 8/1996 | Humes et al. ............................. | 623/11 |
| 5,686,289 | 11/1997 | Humes et al. ....................... | 435/240.2 |

*Primary Examiner*—Michael G. Wityshyn
*Assistant Examiner*—Janet M. Kerr
*Attorney, Agent, or Firm*—Oblon, Spivak, McClelland, Maier & Neustadt, P.C.

[57] ABSTRACT

A novel cell seeded hollow fiber bioreactor is described as a potential bioartificial kidney. Endothelial cells along with pericyte, vascular smooth muscle, and/or mesangial cells or any mesenchymally derived support cells are seeded along a hollow fiber in a perfused bioreactor to reproduce the ultrafiltration function and transport function of the kidney. Maintenance of tissue specific function and ultrastructure suggest that this bioreactor provides an economical device for treating renal failure.

14 Claims, 17 Drawing Sheets

S.P.: SIGNAL PEPTIDE (PAI OR vWF)
SV: SV40 PROMOTER
NEO: NEOMYCIN RESISTANT GENE

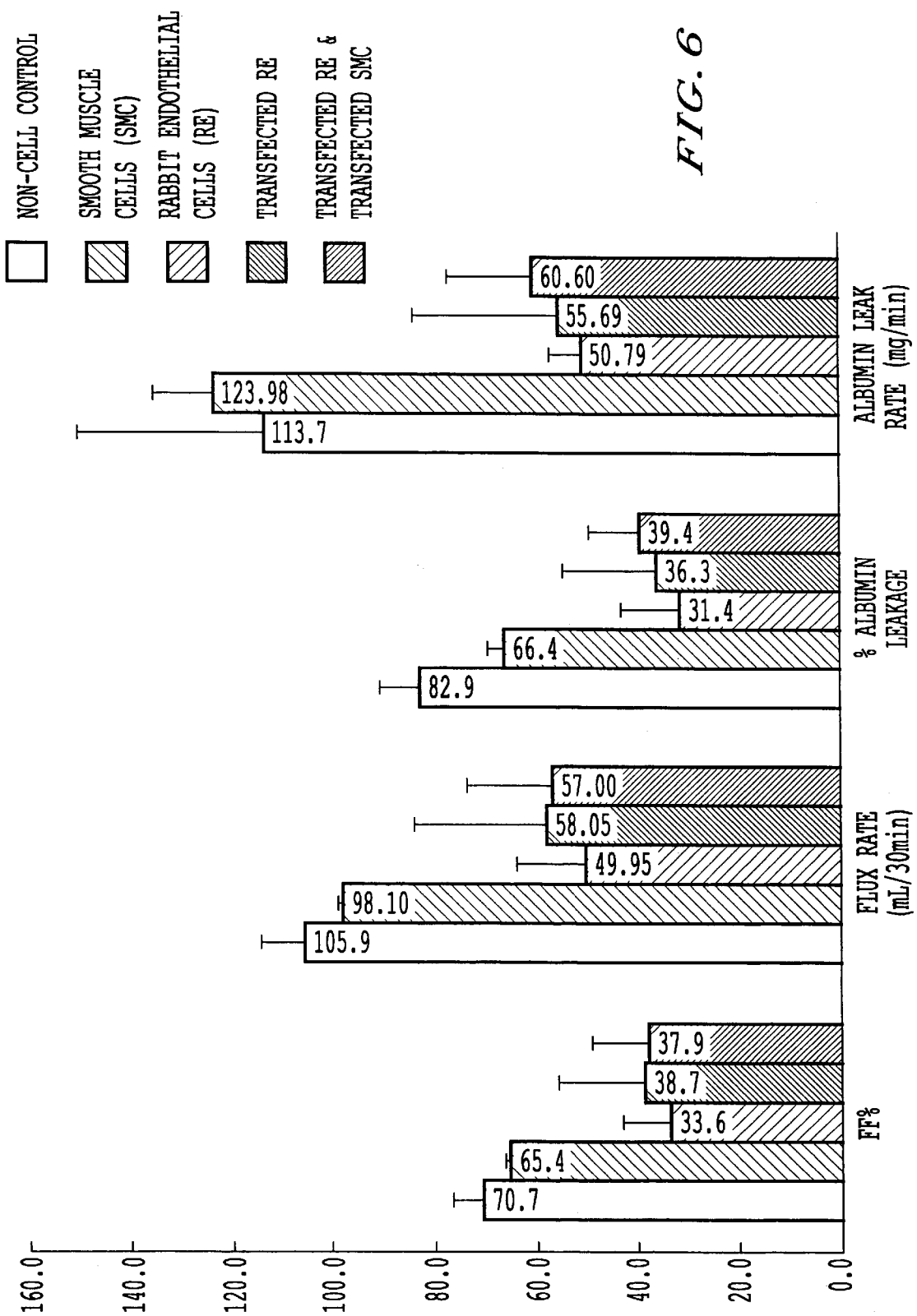

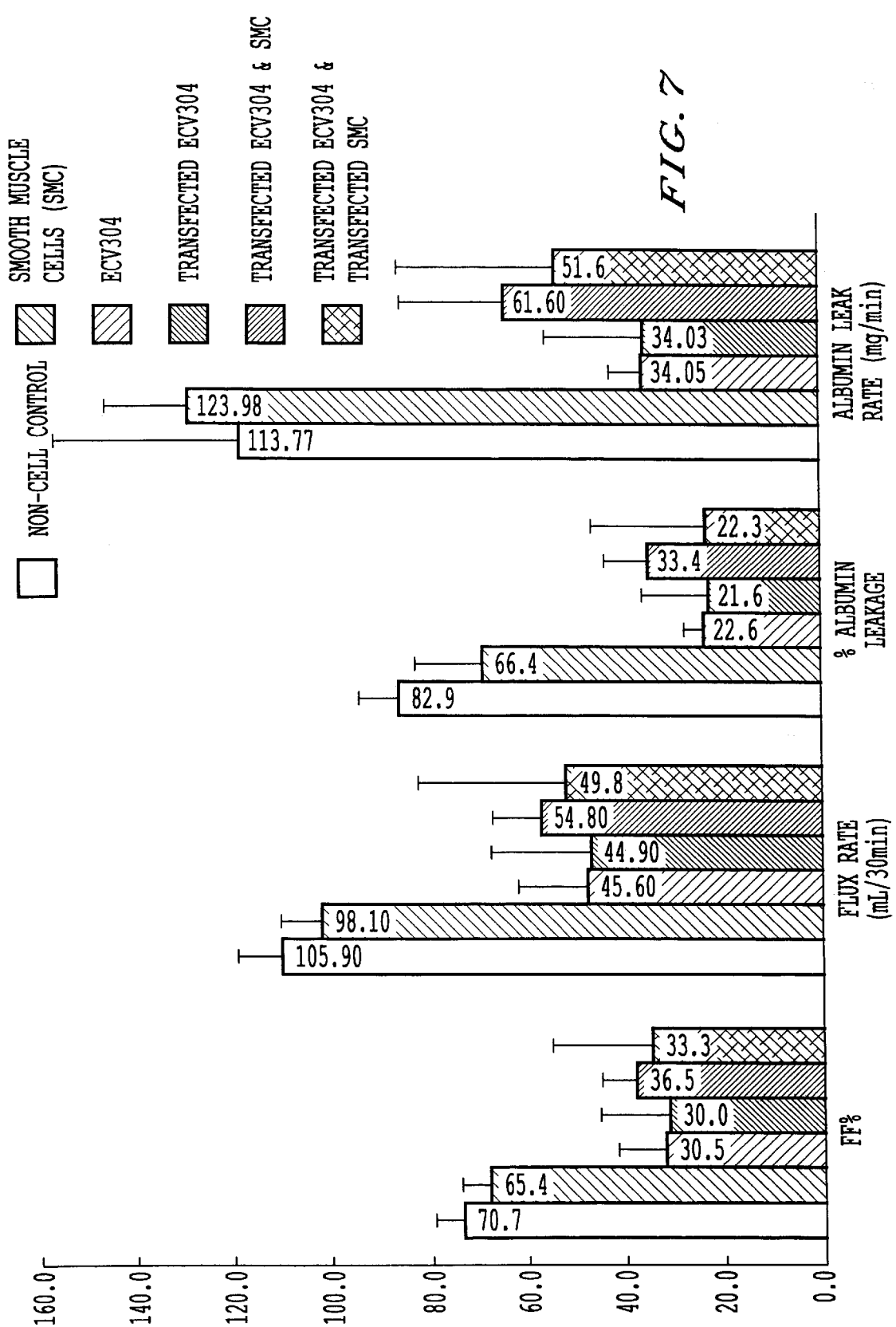

HIRUDIN PRODUCTION

| CELL TYPE | CONDITION | HIRUDIN PRODUCTION (ng) | AVERAGE |
|---|---|---|---|
| TRANSFECTED ECV304 | pLJ4-15 | 224.935<br>335.155<br>188.574 | 249.555 |
| TRANSFECTED ECV304 & TRANSFERED SMC | pLJ4-15/pLJ4-15 | 379.033<br>305.602<br>332.254 | 338.963 |
| TRANSFECTED RABBIT EC (1/23/97) | pLJ2-6 | 226.073<br>462.695<br>375.069 | 354.612 |
| TRANSFECTED RABBIT EC (2/8/97~) | pLJ4-5 | 157.545<br>183.542<br>162.249<br>275.147<br>153.997<br>293.303<br>164.945<br>413.464<br>351.568 | 239.529 |
| TRANSFECTED RABBIT EC & TRANSFECTED SMC (1/23/97) | pLJ2-6/pLJ4-15 | 359.853<br>286.455<br>355.410 | 333.906 |
| TRANSFECTED RABBIT EC & TRANSFECTED SMC (2/8/97~) | pLJ4-5/pLJ4-15 | 225.218<br>311.460<br>176.554<br>269.370<br>214.792 | 239.479 |

FIG. 9A

| FF % | SD | FLUX RATE (mL/min) | SD | % LEAKAGE | SD | LEAK RATE (mg/min) | SD | |
|---|---|---|---|---|---|---|---|---|
| 36.5 | (6.6) | 1.83 | (0.33) | 33.43 | (8.34) | 61.603 | (20.723) | t-ECV304&SMC |
| 30.0 | (13.4) | 1.50 | (0.66) | 21.59 | (13.14) | 34.034 | (19.485) | t-ECV304 |
| 33.3 | (19.7) | 1.66 | (0.98) | 31.56 | (22.28) | 51.607 | (31.096) | t-ECV304&t-SMC |
| 41.5 | (33.2) | 2.08 | (1.66) | 41.35 | (35.22) | 60.134 | (49.312) | t-RE #1 |
| 42.7 | (11.7) | 2.14 | (0.59) | 41.77 | (18.01) | 1.992 | (0.585) | t-RE&t-SMC IgG |
| 37.3 | (11.1) | 1.87 | (0.55) | 33.74 | (11.68) | 53.462 | (22.872) | t-RE #2 |
| 44.0 | (0.5) | 2.22 | (0.02) | 46.10 | (4.95) | 74.421 | (8.079) | t-RE&t-SMC #1 |
| 30.5 | (8.9) | 1.52 | (0.44) | 30.84 | (6.15) | 0.543 | (0.062) | t-RE&t-SMC IgG |
| 37.0 | (11.8) | 1.85 | (0.59) | 38.46 | (10.60) | 58.623 | (17.102) | t-RE&t-SMC #2 |

*FIG. 9B*

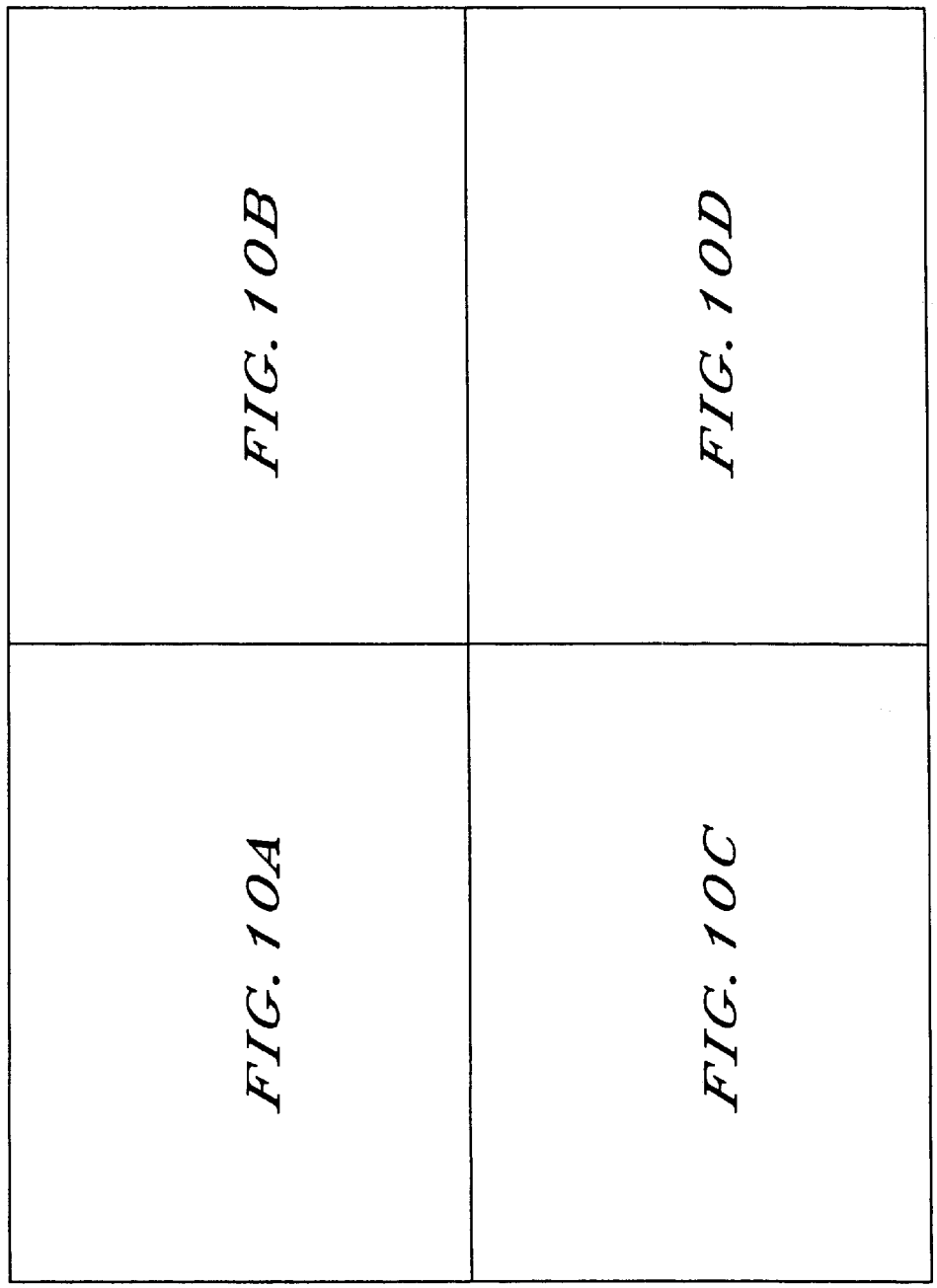

FIG. 10A

CELCO UNIT: ALBUMIN

| SEED DATA | TEST DATA | CELL TYPE | MATRIX | CONDITION | FF % | AVG |
|---|---|---|---|---|---|---|
| 8/13/96 | 8/1&10/8 | CONTROL | | | 70.7 | 70.7 |
| 9/3/96 | 8/27/96 | ECV304 | PRONECTIN-F | | 26.5 | |
| 9/17/96 | 9/17/96 | ECV304 | PRONECTIN-F | RESEED OF 8/13/96 | 28.7 | 30.5 |
| 10/4/96 | 10/20/96 | ECV304 | PRONECTIN-F | RESEED #2 OF 8/13/96 | 36.4 | |
| 8/27/96 | 9/8/96 | RABBIT EC | PRONECTIN-F | | 34.2 | |
| 10/3/96 | 10/3/96 | RABBIT EC | PRONECTIN-F | RESEED OF 8/27/96 | 33.0 | 33.6 |
| 9/19/96 | 9/27/96 | TRANSFECTED ECV304 | PRONECTIN-F | | 45.3 | |
| 9/13/96 | 10/17/96 | TRANSFECTED ECV304 | PRONECTIN-F | RESEED OF 9/13/96 | 36.4 | |
| 10/4/96 | 10/29/96 | TRANSFECTED ECV304 | FIBRONECTIN | | 38.1 | |
| 10/21/96 | 10/31/96 | TRANSFECTED ECV304 | ECAF | | 37.7 | |
| 10/21/96 | 11/7/96 | TRANSFECTED ECV304 | ECAF | RESEED OF 10/21/96 | 11.7 | |
| 11/1/96 | 11/14/96 | TRANSFECTED ECV304 | ECAF | RESEED #2 OF 10/21/96 | 15.4 | |
| 11/7/96 | 11/26/96 | SMC | FIBRONECTIN | | 65.4 | 65.4 |
| 11/12/96 | 11/29/96 | TRANSFECTED ECV304 & SMC | FIBRONECTIN | | 44.0 | |
| 11/14/96 | 12/18/96 | TRANSFECTED ECV304 & SMC | FIBRONECTIN | RESEED OF 11/14/96 | 31.7 | |
| 12/6/96 | 12/19/96 | TRANSFECTED ECV304 & SMC | FIBRONECTIN | | 33.7 | 36.5 |
| 12/6/96 | 1/22/97 | TRANSFECTED ECV304 | PRONECTIN-F | | 40.0 | |
| 1/22/97 | 2/20/97 | TRANSFECTED ECV304 | PRONECTIN-F | QUAD UNIT | 15.4 | |
| 1/22/97 | 2/5/97 | TRANSFECTED ECV304 & TRANSFECTED SMC | PRONECTIN-F | | 47.2 | 30.0 |
| 1/22/97 | 2/20/97 | TRANSFECTED ECV304 & TRANSFECTED SMC | PRONECTIN-F | QUAD UNIT | 19.4 | |
| 1/23/97 | 2/6/97 | TRANSFECTED RABBIT EC | PRONECTIN-F | | 65.0 | 33.3 |
| 1/23/97 | 2/25/97 | TRANSFECTED RABBIT EC | PRONECTIN-F | QUAD UNIT | 18.0 | |

FIG. 10B

| SD | FLUX RATE (mL/min) | AVG | SD | % LEAKAGE | AVG | SD | LEAK RATE (mg/min) | AVG | SD | |
|---|---|---|---|---|---|---|---|---|---|---|
| (5.7) | 3.53 | 3.53 | (0.29) | 82.90 | 82.90 | (7.80) | 113.767 | 113.767 | (36.671) | ECV304 |
| | 1.30 | | | 8.81 | | | 15.988 | | | |
| | 1.44 | | | 23.89 | | | 38.414 | | | |
| (5.2) | 1.82 | 1.52 | (0.27) | 35.10 | 22.60 | (13.19) | 47.611 | 34.004 | (16.266) | RE |
| | 1.68 | | | 29.16 | | | 42.379 | | | |
| (0.8) | 1.65 | 1.67 | (0.02) | 33.72 | 31.44 | (3.22) | 59.207 | 50.793 | (11.899) | |
| | 2.20 | | | 2.62 | | | 6.311 | | | |
| | 1.82 | | | 28.95 | | | 45.225 | | | |
| | 1.95 | | | 33.51 | | | 44.618 | | | |
| | 1.89 | | | 34.99 | | | 55.394 | | | |
| | 0.59 | | | 8.60 | | | 14.991 | | | |
| | 0.77 | | | 15.18 | | | 23.969 | | | |
| (9.4) | 3.27 | 3.27 | (0.47) | 66.43 | 66.43 | (3.62) | 123.978 | 123.978 | (6.761) | SMC |
| | 2.2 | | | 43.06 | | | 85.163 | | | |
| | 1.59 | | | 28.42 | | | 53.443 | | | |
| (6.6) | 1.69 | 1.83 | (0.33) | 28.80 | 33.43 | (8.34) | 46.202 | 61.603 | (20.723) | t-ECV304 & SMC |
| | 2.00 | | | 35.54 | | | 58.742 | | | |
| (13.4) | 0.77 | 1.50 | (0.66) | 13.33 | 21.59 | (13.14) | 23.025 | 34.034 | (19.485) | t-ECV304 |
| | 2.35 | | | 47.31 | | | 73.595 | | | |
| (19.7) | 0.97 | 1.66 | (0.98) | 15.80 | 31.56 | (22.28) | 29.618 | 51.607 | (31.096) | t-ECV304 & t-SMC |
| | 3.25 | | | 66.25 | | | 95.003 | | | |
| | 0.9 | | | 18.44 | | | 25.265 | | | |

FIG. 10C

| SEED DATA | TEST DATA | CELL TYPE | MATRIX | CONDITION | |
|---|---|---|---|---|---|
| 1/23/97 | 2/6/97 | TRANSFECTED RABBIT EC & TRANSFECTED SMC | PRONECTIN-F | | 44.0 |
| 2/8/97 | 2/25/97 | TRANSFECTED RABBIT EC | PRONECTIN-F | | 24.4 |
| 2/8/97 | 3/7/97 | TRANSFECTED RABBIT EC | PRONECTIN-F | | 46.0 |
| 2/11/97 | 2/26/97 | TRANSFECTED RABBIT EC & TRANSFECTED SMC | PRONECTIN-F | | 17.7 |
| 2/11/97 | 3/14/97 | TRANSFECTED RABBIT EC & TRANSFECTED SMC | PRONECTIN-F | | 31.4 |
| 3/14/97 | 3/27/97 | TRANSFECTED RABBIT EC | PRONECTIN-F | | 47.0 |
| 3/14/97 | 4/16/97 | TRANSFECTED RABBIT EC | PRONECTIN-F | QUAD UNIT | 31.7 38.7 |
| 4/16/97 | 4/30/97 | TRANSFECTED RABBIT EC & TRANSFECTED SMC | PRONECTIN-F | QUAD UNIT | 32.0 |
| 4/16/97 | 4/30/97 | TRANSFECTED RABBIT EC & TRANSFECTED SMC | PRONECTIN-F | QUAD UNIT | 34.0 |
| 4/16/97 | 5/7/97 | TRANSFECTED RABBIT EC & TRANSFECTED SMC | PRONECTIN-F | QUAD UNIT | 49.0 |
| 4/16/97 | 5/1/97 | TRANSFECTED RABBIT EC & TRANSFECTED SMC | PRONECTIN-F | P-P | 42.7 |
| 4/16/97 | 5/8/97 | TRANSFECTED RABBIT EC & TRANSFECTED SMC | PRONECTIN-F | | 52.0 37.9 |

CELCO UNIT: IgG

| SEED DATA | TEST DATA | CELL TYPE | MATRIX | CONDITION | FF % | AVG |
|---|---|---|---|---|---|---|
| | 3/27&4/1 | CONTROL | PRONECTIN-F | | 67.4 | 67.4 |
| 3/14/97 | 4/1/97 | TRANSFECTED RABBIT EC | PRONECTIN-F | QUAD UNIT | 51.0 | 42.7 |
| 3/14/97 | 4/28/97 | TRANSFECTED RABBIT EC | PRONECTIN-F | QUAD UNIT | 34.4 | |
| 4/16/97 | 5/14/97 | TRANSFECTED RABBIT EC & TRANSFECTED SMC | PRONECTIN-F | P-Q #1 | 41.7 | |
| 4/16/97 | 5/21/97 | TRANSFECTED RABBIT EC & TRANSFECTED SMC | PRONECTIN-F | P-Q #2 | 33.0 | |
| 4/16/97 | 5/19/97 | TRANSFECTED RABBIT EC & TRANSFECTED SMC | PRONECTIN-F | Q-Q #1 | 25.7 | 30.5 |
| 4/16/97 | 5/28/97 | TRANSFECTED RABBIT EC & TRANSFECTED SMC | PRONECTIN-F | Q-Q #2 | 21.4 | |

FIG. 10D

| FLUX RATE (mL/min) | | | % LEAKAGE | | | |
|---|---|---|---|---|---|---|
| SD | AVG | SD | | AVG | SD | |
| | 2.22 | | 46.10 | | | |
| | 1.22 | | 21.67 | | | |
| | 2.3 | | 45.45 | | | |
| | 0.88 | | 18.20 | | | |
| | 1.57 | | 30.20 | | | |
| | 2.35 | | 41.85 | | | |
| (17.3) | 1.59 | 1.94 (0.86) | 25.97 | 36.27 | (18.58) | t-RE |
| | 1.6 | | 40.16 | | | |
| | 1.7 | | 45.35 | | | |
| | 2.45 | | 43.96 | | | |
| | 2.14 | | 43.35 | | | |
| (11.2) | 2.6 | 1.90 (0.56) | 48.00 | 39.42 | (10.18) | t-RE & t-SMC |

| FLUX RATE (mL/min) | | | % LEAKAGE | | | LEAK RATE (mg/min) | | | |
|---|---|---|---|---|---|---|---|---|---|
| SD | AVG | SD | | AVG | SD | | AVG | SD | |
| (10.4) | 3.37 | 3.37 (0.52) | 64.60 | 64.60 | (8.34) | 3.156 | 3.156 | (0.410) | |
| | 2.55 | | 54.50 | | | 2.406 | | | |
| (11.7) | 1.72 | 2.14 (0.59) | 29.03 | 41.77 | (18.01) | 1.578 | 1.992 | (0.585) | t-RE |
| | 2.08 | | 27.47 | | | 0.535 | | | |
| | 1.65 | | 38.80 | | | 0.588 | | | |
| | 1.29 | | 32.29 | | | 0.59 | | | |
| (8.9) | 1.07 | 1.52 (0.44) | 24.79 | 30.84 | (6.15) | 0.458 | 0.534 | (0.062) | t-RE & t-SMC |

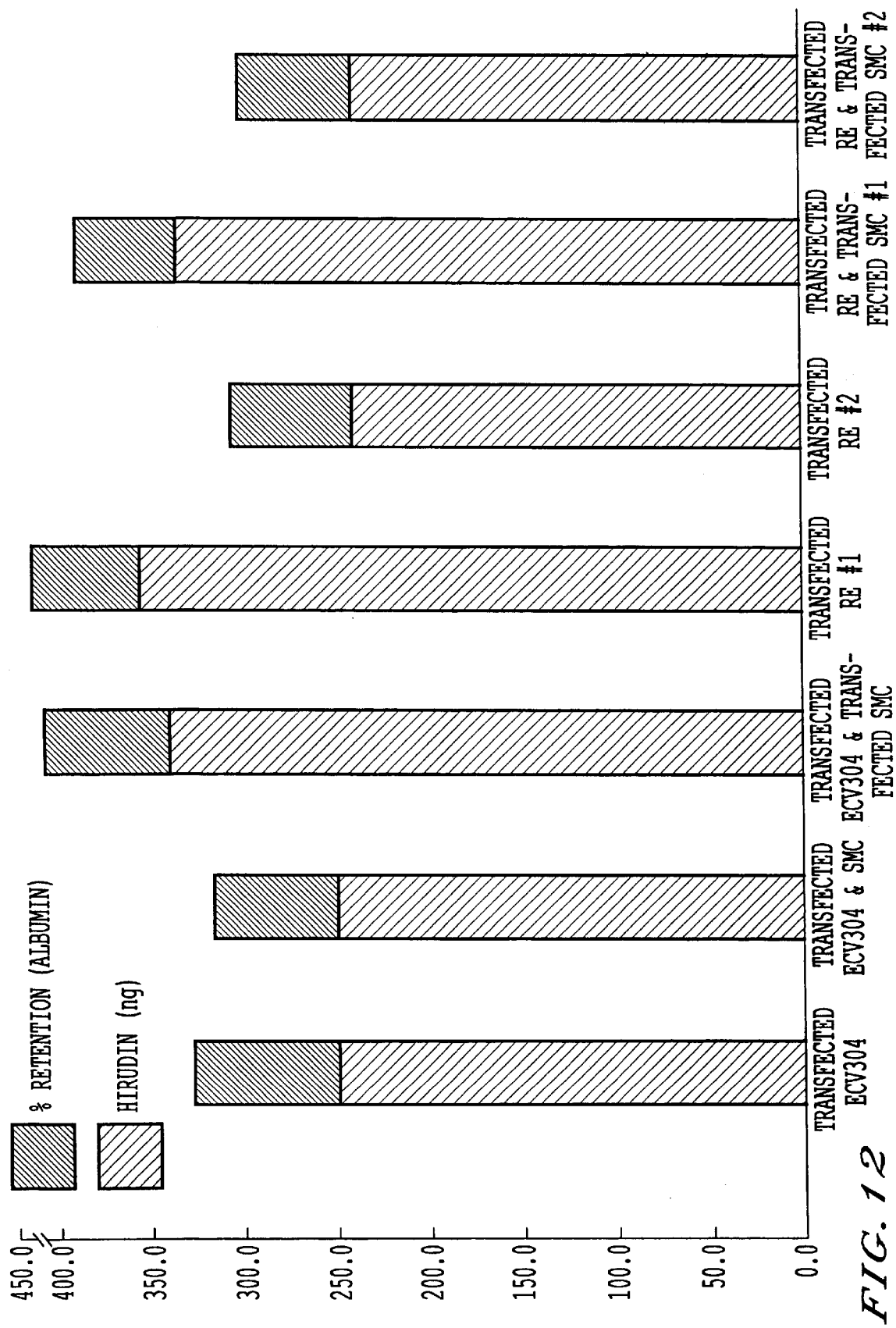

METHODS AND COMPOSITIONS OF A BIOARTIFICIAL KIDNEY SUITABLE FOR USE IN VIVO OR EX VIVO

Applicants hereby claim as priority U.S. Provisional Application Ser. No. 60/027,495 filed on Sep. 30, 1996.

Work on this invention was supported by National Institutes of Health Grant No. DK30819. The Government has certain rights in the invention.

BACKGROUND OF THE INVENTION

1. Field of the Invention

The present invention provides a BIOARTIFICIAL kidney comprising (1) a filtration device comprising endothelial cells and pericyte cells and (2) a tubule processing device.

2. Background of the Invention

An implantable epithelial cell system derived from immortalized cells grown as confluent monolayers along the luminal surface of impermeable polymeric hollow fibers has been described as a first step for tubule functional replacement (Ip and Aebischer, *Artificial Organs* 13:58–65, 1989, incorporated herein by reference). Unfortunately, immortalized cells do not possess the full range of function of primary renal cells. Critical to development of functional renal tissue is the isolation and growth in vitro of primary cell lines. Primary cell lines should possess characteristics such that they exhibit a high capacity for self renewal. Preferably, the primary cell lines should possess stem cell-like characteristics such that they have the ability to differentiate under defined conditions into specialized cells having the correct structure and functional components of a physiologic kidney (Hall and Watt, *Development* 106:619–633, 1989; Potten and Loeffler, *Development* 110:1001–1020, 1990; Garlick et al., *J. Invest. Dermatol.* 97(5) :824–829, 1991; all incorporated herein by reference).

Prior to the contributions of the present inventors, primary cells could not be maintained for a sufficient time to make their use in bioengineering applications useful. The present inventors discovered methodology to isolate and grow renal tubule stem or progenitor cells from mammalian kidneys (U.S. Pat. No. 5,429,938; Humes and Cieslinski, *Exp. Cell Res.* 201:8–15, 1992; incorporated herein by reference).

Non-serum containing growth conditions were identified which select for tubule cells with a high capacity for self renewal and an ability to differentiate phenotypically, collectively and individually, into tubule structures in collagen gels. Genetic marking of the cells with a recombinant retrovirus containing the lac-Z gene and dilution analysis demonstrated that in vitro tubulogenesis arose from clonal expansion of a single genetically tagged progenitor cell. Thus, a population of tubule cells resides within the kidney which exists in a relatively dormant, slowly replicative state, but which retains a rapid potential to proliferate, differentiate and undergo pattern formation to regenerate the tubule epithelium of the lining of the kidney following severe ischemic or toxic injury.

Ex vivo studies on these renal tubule progenitor cells have demonstrated that a mixture of (i) TGF-α or EGF and (ii) retinoic acid (RA) can promote differentiation of these cells into renal tubules (Humes and Cieslinski, *Exp. Cell Res.* 201:8–15, 1992). Thus, a coordinated interplay between growth factors and retinoids appears to be required to induce pattern formation and morphogenesis. Using immunofluorescence microscopy, it has also been demonstrated that retinoic acid induces laminin A and B1 chain production in these cells and that purified soluble laminin can be completely substituted for retinoic acid in kidney tubulogenesis (Humes and Cieslinski, supra). Retinoic acid, as a morphogen, appears to promote pattern formation and differentiation by regulating the production of an extracellular matrix molecule.

Using this technology, the present inventors have described implantable bioartificial kidney devices (U.S. Ser. No. 08/133,436), which can replace renal function and as a result can circumvent the need for long-term dialytic therapy, would substantially benefit patients suffering from ESRD by increasing life expectancy, increasing mobility and flexibility, increasing quality of life, decreasing the risk of infection, and reducing therapy costs.

The present invention describes bioartificial devices with improved durability.

SUMMARY OF THE INVENTION

One object of the present invention is to provide a bioartificial kidney device with a longer lifetime than previous devices.

The present inventors have now achieved this object, by combining hollow fiber technology with renal cell technology. In particular, the present inventors have found that porous hollow fibers can be seeded with renal cells such as endothelial, epithelial, pericyte, vascular smooth muscle cells, mesangial cells or any mesenchymally derived support cells to obtain devices which mimic the various biological functions of the kidney.

BRIEF DESCRIPTION OF THE FIGURES

FIG. 6 is a bar graph illustrating filtration fraction (FF)%, flux rate (ml/30 min), % albumin leakage and albumin leak rate (mg/min) for rabbit endothelial cells (RE).

FIG. 7 is a bar graph illustrating filtration fraction (FF)%, flux rate (ml/30 min), % albumin leakage and albumin leak rate (mg/min) for ECV304 cells.

FIG. 9 shows hirudin production of various transfected cells, as well as filtration fraction (FF)%, flux rate (ml/30 min), % leakage and leak rate (mg/min).

FIG. 10 shows filtration fraction (FF)%, flux rate (ml/30 min), % leakage and leak rate (mg/min) of various transfected cells with different matrices.

FIG. 12 is a bar graph showing % retention and hirudin production of various transfected cells.

DETAILED DESCRIPTION OF THE PREFERRED EMBODIMENTS

Figure 1:
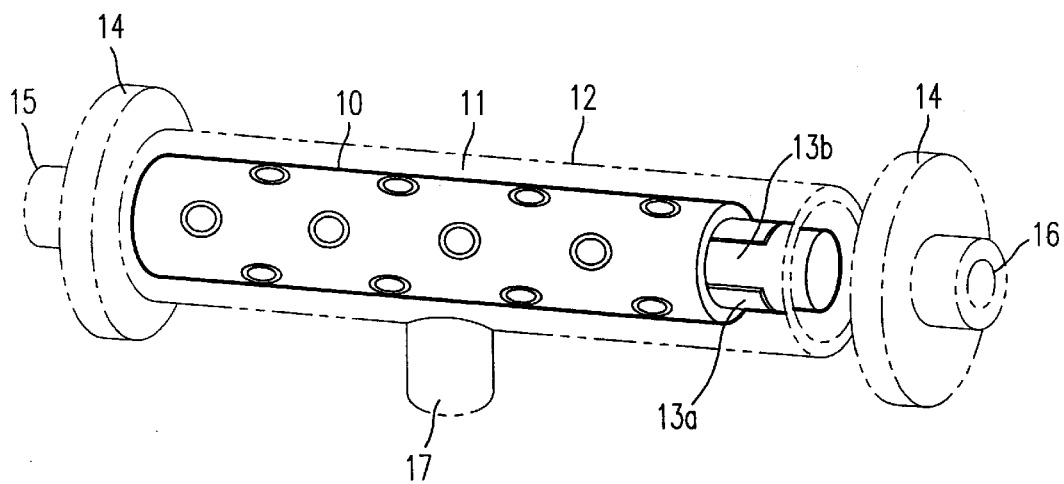
FIG. 1 is a schematic of the preferred embodiment of a bioartificial filtration device in accordance with the present invention.

The present inventors have found that a population of cells resides in the kidney which has retained the capacity to proliferate and morphogenically differentiate into tubule structures in vitro. These cells are hereinafter referred to as renal stem cells.

Renal stem cells retain a high capacity for self renewal and an ability to differentiate phenotypically, collectively and individually, into tubule structures and other cell types. The inventors have identified non-serum containing growth conditions that select for these renal stem cells.

The following definitions are adapted from "The Kidney", 4th ea., Vol. I, Brenner & Rector, ed. W B Saunders Co., Harcourt Brace Jovanovich, Inc., Philadelphia, 1991, in particular, chapter 3 and Freshney, in "Culture of Animal Cells: A Manual of Basic Technique", 2nd ea., Wiley-Liss, New York, 1987, in particular chapters 1, 2 and 15; incorporated herein by reference.

Passaging, or "subculturing", occurs when a primary cell culture is subdivided and part is transferred into fresh culture media. Techniques for passaging are known in the art and are described, for example, by Freshney, in "Culture of Animal Cells: A Manual of Basic Technique", 2nd ea., Wiley-Liss, New York, 1987.

Primary culture means a freshly isolated culture of cells derived directly from a particular organ, tissue or the blood of an organism. Primary cells cultures are usually heterogenous and have a low growth fraction, but they are representative of the cell types in the tissue from which they were derived. Passaging of the primary culture gives rise to a secondary culture.

The formation of a cell line from a primary culture implies: (1) an increase in total cell number over several generations: (2) that cells or cell lineages with similar growth capacity will predominate; resulting in (3) a degree of uniformity in the cell population. The line may be characterized, and those characteristics will apply for most of its finite lifespan. The derivations of "continuous" (or "established") cell lines usually implies a phenotypic change or "transformation".

Monolayer culture signifies that the cells will attach to the substrate given the opportunity and that normally the cells will be propagated in this mode.

Immortalized cells result from transformation in vitro of a cell line induced spontaneously, chemically or virally. Transformation implies a phenotypic modification not necessarily involving the uptake of new genetic material, such as is seen for transfection. Continuous cell lines are usually aneuploid and often have a chromosome complement between the diploid and tetraploid value. Most normal cells have a finite life-span of 20–100 generations but some cells, notably from tumors, can produce continuous cell lines with an infinite life span.

Cells from many segments of the nephron have been grown in primary culture (see for example, Handler & Burg in "Application of tissue culture techniques to study of renal tubular epithelia" in Windhager & Giebisch (eds):Handbook of Physiology, Section 8, Renal Physiology, American Physiological Society, Williams & Wilkins, Baltimore). Specific cells have been separated on the basis of differential growth, by mechanical dissection, by differential centrifugation and with the aid of specific antibodies (immunodissection).

The present inventors have found that porous hollow fibers can be seeded with renal cells such as endothelial, epithelial, pericyte, vascular smooth muscle and mesangial cells to obtain devices which mimic the various biological functions of the kidney.

Filtration Device

The filtration device according to the present invention comprises a device for purifying blood and suitably comprises either a single semipermeable hollow fiber or a collection of semipermeable hollow fibers in which are coated, either externally or internally, with a layer of extracellular matrix (ECM) upon which either may or may not be grown a population of cells such as a confluent monolayer of endothelial cells and/or a layer of pericyte, vascular smooth muscle or mesangial cells. Alternatively, the cells or matrix may be incorporated directly within or on the polymeric structure of the semipermeable hollow fiber during manufacture (as described hereinafter).

Pericyte cells, preferably mesangial cells, are optionally present either in a separate layer between the ECM and the monolayer of epithelial and/or endothelium cells or in a mixture with the epithelial and/or endothelium cells.

In a preferred embodiment, a monolayer of endothelial cells and pericyte cells is seeded on the fiber.

The filtration device of the present invention promotes ultrafiltration of blood via convective transport of water and solutes out of the blood and across the wall of a semipermeable hollow fiber with high hydraulic permeability. Filtration of blood by a convective process has several distinct advantages: it imitates the glomerular process of toxin removal with increased clearance of higher molecular weight solutes and removes all solutes up to a selected molecular weight cutoff at the same rate. Convective transport occurs independently of the existing concentration gradient and depends predominantly on the hydraulic pressure gradient across the membrane.

In a preferred embodiment of the invention, FIG. 1 illustrates a filtration device comprising at least one hollow fiber 10 in a chamber 11 defined by a housing 12. The hollow fiber 10 is internally coated with various extracellular matrix components 13a upon which is grown a confluent monolayer comprising endothelial cells and pericyte cells 13b. Both ends of the hollow fiber 10 are cut flush to access the internal compartment of the hollow fiber. The hollow fiber 10 is then snugly fit against headers 14 using any known techniques, for example potted at both ends with potting material. Perfusion inlet port 15 and perfusion outlet port 16 are connected to the headers 14 at opposite ends. The housing is further elaborated with filtrate outlet port 17.

Blood containing undesirable impurities such as metabolic waste flows from the patient's arterial lumen, enters perfusion inlet port 15, passes through hollow fiber 10, exits through perfusion outlet port 16, whereupon it is reabsorbed into the vascular venous flow. As blood passes through the fiber, filtrate proceeds through confluent monolayer 13b, extracellular matrix 13a and the wall of hollow fiber 10, into the collecting chamber 11. Filtrate exits collecting chamber 11 through filtrate outlet port 17.

The filtration device is preferably composed of a large number of hollow fibers bundled together. This arrangement improves the surface area available for capillary interface with the hollow fiber bundle. In one embodiment, the hollow fibers are assembled as a cylindrical array with any number of hollow fibers, approximately 100–10,000 hollow fibers, measuring any suitable length, such as from 1–100 cm in length, being fixed, e.g., potted with potting material, on both ends. The fluid flows from the capillary lumen through the hollow fibers, through the walls of the fibers, into the lumen of the hollow fibers, and exits through filtrate outlet port.

Anticoagulants can be introduced into the blood within the filtration unit. Suitable anticoagulants include those known in the art such as heparin and hirudin. Preferably, hirudin, hirulogs and fragments thereof which retain anticoagulant activity are used. To date, there are about 12 variants of hirudin, as well as hirudin fragments and hirulog compounds (Maraganore et al., *J. Biol. Chew.* 264; 8692–8698, 1989; Scharf et al., *FIBS* 255; 105–110, 1989; Maraganore et al., *Biochemistry* 29; 7095–7101, 1990). Suitable hirudin fragments useful in this embodiment include fragments which contain the catalytic site of hirudin, which blocks platelet aggregation, as well as the fibrinogen binding site, which blocks activation of coagulation (Maraganore et al, 1989, supra; Maraganore et al., 1990, supra; Borbon et al., *FIBS* 294:163–166, 1991).

These anticoagulants can suitably be introduced via exogenous administration via subcutaneous infusion port connected to the internal compartments of the hollow fibers. Alternatively, the semipermeable fibers can be internally coated with a layer of immobilized anticoagulant compounds, preferably peptides. These compounds can either be absorbed onto the polymer or covalently attached to the polymer using conventional techniques (Andrade et al., *Adv. Polymer Sci.* 79:1–63, 1986; Lin et al., Biomaterials 13:905–913, 1992; Hubbel et al., Biotechnology 9:568–572, 1991). Covalently attached peptides can serve an additional function of increasing endothelial cell adhesion to the semipermeable fiber (Lin et al., supra, Hubbell et al, supra).

Alternatively, endothelial cells can be transfected with various genes which encode these compounds (Flugelman et al ., *Circulation Research* 70:348–354, 1992; Dichek et al., *Circulation* 80:1347–1353, 1989). In a preferred embodiment, the endothelial cells coating the fiber are transfected with cDNA encoding for hirudin or hirulog compounds and express these compounds either on the external surface of their membranes or secrete these compounds. DNA from synthesized oligonucleotides and polymerase chain reaction techniques can be obtained and code for these types of derivatives. Using this cDNA stable gene transfection with these oligonucleotides can be used to induce local production of anticoagulants along the lining layer of endothelium. Stable gene transfection with vectors containing these oligonucleotides can be achieved with conventional methods (Sambrook et al., "*Molecular Cloning: A Laboratory Manual*", 2nd ed. Vols 1–3, Cold Spring Harbor Laboratory, N.Y., 1989). DEAE dextran can be used to improve transfection of DNA encoding hirudin as described by (Dichek et al, *Blood* 77:533–541, 1991; Jaklitsch et al., *J Cell Physiol.* 154:207–216, 1993). Preferably, transfection is achieved using recombinant retroviruses. In order to ensure that hirudin, hirulogs, or hirudin fragments will be secreted from the cell, a signal peptide appropriate for secretion and cleavage or membrane binding peptide is preferably incorporated into the vectors. In an alternate preferred embodiment, the filtration device can contain both nontransduced and transfected endothelial cells.

Suitable semipermeable hollow fibers useful in accordance with the present invention can be composed of any known biocompatible polymer including CUPROPHAN (a cellulose regenerated by means of the cuprammonium process, available from Enka), HEMOPHAN (a modified CUPROPHAN with improved biocompatibility, available from Enka), CUPRAMMONIUM RAYON (a variety of CUPROPHAN, available from Asahi), BIOMEMBRANE (cuprammonium rayon available from Asahi), saponified cellulose acetate (such as fibers available from Teijin or CD Medical), cellulose acetate (such as fibers available from Toyobo (Nipro)), cellulose (such as those regenerated by the modified cuprammonium process or by means of the viscose process, available from Terumo or Textikombinat (Pirna, GDR) respectively), polyacrylonitrile (PAN), polysulphone, acrylic copolymers (such as acrylonitrile-NA-methallyl-sulfonate copolymer, available from Hospal), polycarbonate copolymer (such as GAMBRONE, a fiber available from Gambro), polymethylmethacrylate copolymers (such as fibers available from Toray) and ethylene vinyl copolymer (such as EVAL, a ethylene-vinyl alcohol copolymer available from Kuraray). Preferably, polysulphone fibers are used. Other suitable biocompatible fibers are disclosed by Salem and Mujais, In *Dialysis Therapy*, ch. 5, 2nd ea., Nissenson and Fine, Eds., Hanley & Belfus, Inc., Pennsylvania, 1993 and Sigdell, Artificial Organs, 12(4):345, 1988; incorporated herein by reference.

The hollow fibers must have high hydraulic conductivity, as measured in terms of the ultrafiltration coefficient. Suitably, the ultrafiltration coefficient is greater than 20 mL/hr,Torr,m2, preferably 20–100 mL/hr,Torr,m2. The hollow fibers suitably have a molecular weight cutoff, or pore size, which is less than or equal to 60,000 g/mol. Microporous fibers may also be used.

The internal and/or external surface of the hollow fiber is precoated with suitable extracellular matrix (ECM) components including Type I collagen, Type IV collagen, laminin, Matrigel, proteoglycan (such as heparin sulfate and dermatan sulfate) fibronectin, and combinations thereof to form an ECM layer.

Once an ECM layer has been established on the surface(s) of the hollow fiber, this layer is then seeded with endothelial cells and pericyte, vascular smooth muscle or mesangial cells. The cells may be seeded inside and/or outside of the hollow fiber.

Alternatively, pericyte, vascular smooth muscle or mesangial cells can be first seeded on the ECM layer and allowed to reach confluence. Thereafter, endothelial cells can be seeded.

Endothelial and pericyte cells according to the present invention can be cultured using known techniques. Preferably, cells which are autologous to the patient are used. Preferably, the initial culture comprises 50%, based on the total number of cells in culture, pericyte cells and 50% endothelial and/or epithelial cells.

Mesangial cells are typically seeded at a density of at least $1 \times 10^7$ cells/mL. The endothelial cells are typically seeded at a density of at least 1×10⁷ cells/mL. The cells can be grown in any suitable media, such as RPMI with 1020% Fetal Calf Serum and Endothelial Cell Growth Supplement (ECGS).

Pericyte cells are described by Sims in *Can. J. Cardiol.* 7(10):431–443 (1991) and Shepro et al in *FASEB J.* 7:1031–1038 (1993), incorporated herein by reference.

Mesangial cells, the preferred type of pericyte cell, are described by Davies in Kidney International, 45:320–327 (1994), incorporated herein by reference.

Cells are seeded into each hollow fiber contained within the filtration device. The cells are then cultured on the ECM layer until a confluent layer is established along the interior of the hollow fiber. Suitable culturing techniques useful for seeding these cells on the surface of the fiber are described by Scott et al., *J. Cell Sci.* 105:269–273, 1993; Schneider et al., Surgery 103:456–462, 1988; Kadletz et al., *J. Thoracic and Cardiovascular* Surgery 104:736–742,1 1992; Shepard et al., Surgery 99: 318–3~6, 1986; and Demetriou et al., *Science* 23:1190–1192, 1986.

Suitable potting material useful for attaching the semipermeable hollow fibers into the chamber of the filtration device include polyurethane, silicon or any elastomeric substance which is biocompatible.

The remaining elements of the device may be made of any known biocompatible material(s).

The filtration device can be suitably implanted either subcutaneously, on the peritoneal membrane, or within various tissues (such as muscle or kidney) or iliac fossa. Alternatively, the filtration device may be located outside the body.

Tubule Processing Device

A first embodiment of the tubule processing device according to the present invention comprises a single hollow fiber seeded with living renal tubule cells on its external or internal surface.

Figure 2:
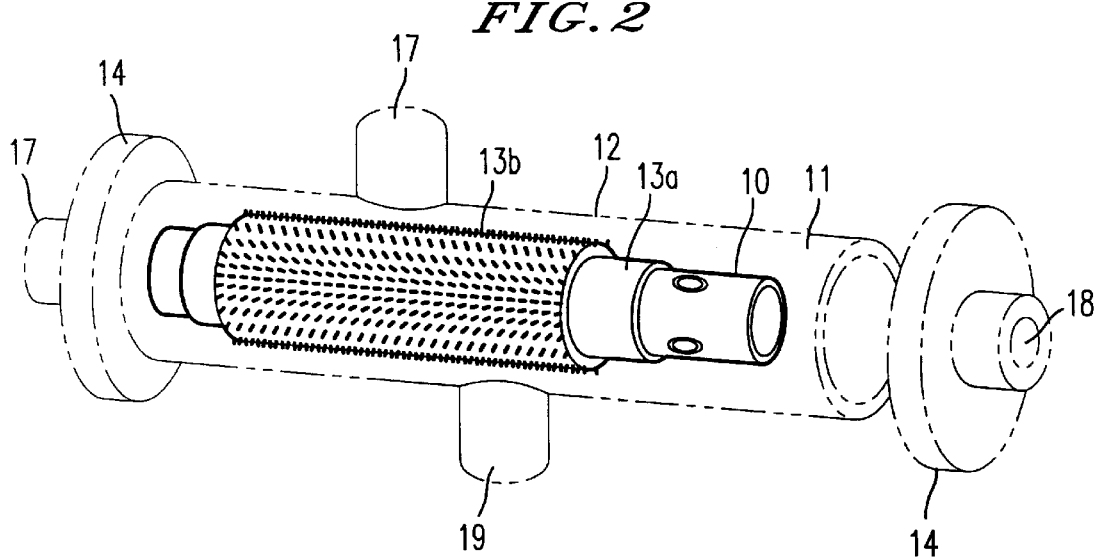
FIG. 2 is a schematic of the preferred embodiment of a bioartificial tubule processing device in accordance with the present invention.

FIG. 2 illustrates the preferred tubule processing device comprising at least one hollow fiber 10 externally coated with a layer of ECM 13b and renal tubule cells 13a in a chamber 11 defined by a housing 12. Both ends of hollow fiber 10 are cut flush so that the resulting access to the lumen of hollow fiber can be attached to postfiltered blood inlet port 17 attached to a header 14 and a blood outlet port 18 attached to a header 14.

Ultrafiltrate from filtered blood is delivered from a filtration device into the chamber surrounded by the housing through the inlet port 17 and exits through urine outlet port 19. As filtrate passes through the chamber, reabsorbent proceeds through confluent monolayer of renal tubule cells 13b, extracellular matrix 13a and the wall of hollow fiber 10, into the lumen of the fiber 10.

The tubule processing device is preferably composed of a large number of hollow fibers bundled together. This arrangement improves the surface area available for capillary interface with the hollow fiber bundle. In one embodiment, the hollow fibers are internally coated with a confluent monolayer of renal tubule cells. The fibers are assembled as a plate with any number of hollow fibers, approximately 100–10,000 hollow fibers, measuring any suitable length, such as from 1–2000 cm in length, being fixed, e.g., potted with potting material, on both ends. One end of each fiber is attached to a filtrate inlet port and the opposite end is attached to a urine outlet port.

Ultrafiltrate flows into a filtrate inlet port through the hollow fibers and over the renal tubule cells. Fluid which is reabsorbed by the cells passes through the semipermeable fibers and back into the systemic circulation. Ultrafiltrate which is not absorbed exits through a urine outlet port.

A bundle of hollow fibers are preferably assembled in a cylindrical array with any number of hollow fibers having the same length, approximately 100–10,000 hollow fibers, measuring any suitable length, such as from 1–2000 cm in length, preferably fixed, for example, with potting material on both ends.

Suitable materials useful for constructing the semipermeable hollow fibers in the tubule processing unit according to the present invention are similar to those described above for the filtration unit.

Renal proximal tubule reabsorption is based upon active $Na^+$ transport which develops a small degree of luminal hypotonicity, resulting in a transepithelial osmotic gradient to drive isotonic fluid reabsorption. Proximal tubule reabsorption is based upon a membrane system with a high diffusive water permeability, low ultrafiltration rate, and a pore size with very low molecular weight cutoff. A suitable hollow fiber cell culture module is commercially available from Cellco (Germantown, MAGNETIC DISK) and comprises a hollow fiber cartridge based upon cellulose membranes with high diffusive water permeability, low ultrafiltration coefficient, and a pore size with molecular weight cutoff of 4,000 daltons. Alternatively, semipermeable fibers which have pore sizes which-are decreased or increased in comparison to the filtration unit can be used. Preferably the pore size (or molecular weight cutoff) is no greater than about 70,000 g/mol, a pore size which prevents antibodies from penetrating into the fibers. The hydraulic pressure within the semipermeable fibers of the tubule processing unit is suitably lower than that of the filtration unit, preferably less than about 10 mmHg. The hydraulic pressure within the tubule processing unit can suitably be controlled by varying the length, size and inner diameter of the conducting conduit which attaches the filtration unit to the tubule processing unit.

The hollow fibers useful in the tubule processing device are seeded with renal tubule epithelial cells. Cells grown within the hollow fiber are immunoprotected from the bloodstream due to the impenetrance of immunologically competent cells through the hollow fiber. Rejection of transplanted cells will, therefore, not occur, in this configuration.

Epithelial renal cells are suitably obtained and cultured using conventional techniques as described in Humes et al., *Exp Cell Res.* 201:8–15; Taub et al., *J. Biol. Chem.*, 254, 11440–11444; Taub et al., *J. Cell Physiol.*, 106 191–199; Taub et al., it. *Supramol. Struct.*, 11, 207–216; Taub et al., *Cell Physiol.*, 105, 369–378; Taub et al., *Proc. Natl. Acad. Sci. USA*, 76, 3338–3342; Taub et al., *Ann. New York Acad. sci.*, 372, 406–421; Taub et al., *J. Supramol. Struct.*, 15, 63–72; and Taub et al., *J. Cell Physiol.*, 114,153–161; which are all incorporated herein by reference.

Cultured cells can be seeded on water and solute permeable membranes precoated with various biomatrix materials, so that the expression of differentiated vectorial transport, metabolic, and endocrinologic function is attained. immunoprotection of the cultured progenitor cells is achieved concurrent with long-term functional performance as long as conditions support tubule cell viability. Cultured cells seeded on the exterior of the hollow fibers are immunoprotected by the housing surrounding the hollow fiber.

Renal tubule progenitor cells can be induced to differentiate morphogenically by culturing them in hormonally-defined cultures as described by Humes and Cieslinski in *Exp. Cell Res.* 201:8–15, 1992, incorporated herein by reference. Differentiation of renal tubule progenitor cells can be induced with (1) EGF and/or TGF-α and (2) RA in 3-dimensional collagen gels.

A hormonally-defined renal cell culture is treated with epidermal growth factor and all-trans retinoic acid. This treatment transforms a confluent monolayer of renal tubule cells into epithelial cell aggregates containing lumens, bordered by cells with a differentiated polarized epithelial cell phenotype. If the ECM layer is either absent or not well developed, transforming growth factor can be added to the culture to promote tubulogenesis.

When necessary, transforming growth factor-α is suitably administered to achieve a concentration of from 0.1 ng/ml–1 mg/ml, epidermal growth factor in a concentration range of from 0.1 nM to 1 μM, and all-trans retinoic acid in a concentration range of from 0.01 μM to 100 μM.

Soluble factors can optionally be added to the renal tubule stem cell culture. Preferred soluble factors include, but are not limited to, fetal calf serum, prostaglandins, hydrocortisone triiodothyronine, selenium, fibroblastic growth factor, transforming growth factor-α, hepatocyte growth factor, and combinations thereof. These soluble factors are preferably added in the following concentrations: fetal calf serum, 3–25% (volume/volume) of growth media; prostaglandin E1, 1 to 100 ng/ml; triiodothyronine, 0.1 nM to 1 μM; selenium, 0.001 to 1.00 μM; cholesterol, 1.0 nM to 0.10 μM; transferrin, 1 to 50 μg/ml; transforming growth factor-α, 0.1 nM to 1μM; insulin, 1–50 μg/ml; hydrocortisone, 1 nm to 1 μM; and hepatocyte growth factor 0.1 ng/ml to 100 ng/ml.

Insoluble factors can additionally be added to the renal tubular stem cell culture.

These insoluble factors include, but are not limited to, a variety of extracellular matrix molecules such as Type I collagen, Type IV collagen, laminin, proteoglycans, fibronectin, and combinations thereof. These insoluble factors are preferably added in the following concentrations: collagen, Type I, 1 to 5 mg/ml, collagen, Type IV, 0.01 to 5 mg/ml; laminin, 10 to 1000 μg/ml; heparin sulfate, 10 to 1000 μg/ml.

Suitable filtration rates in accordance with the present invention may be varied depending upon the need of the patient but are typically of from 10–15 ml/minute of blood through the filtration and tubule processing devices in adult humans. This filtration rate is compatible with life as proven in clinical states of renal insufficiency without dialytic support.

This rate forms 14–15 liters of filtrate per day. The reabsorption rate of the tubule device is at least 50% of the amount which is presented. This rate can be adjusted by increasing the number or length of hollow fibers in the tubule processing device.

The tubule processing device is suitably implanted either subcutaneously, within the peritoneal cavity, or within the iliac fossa.

Bioartificial Kidney

Figure 3:
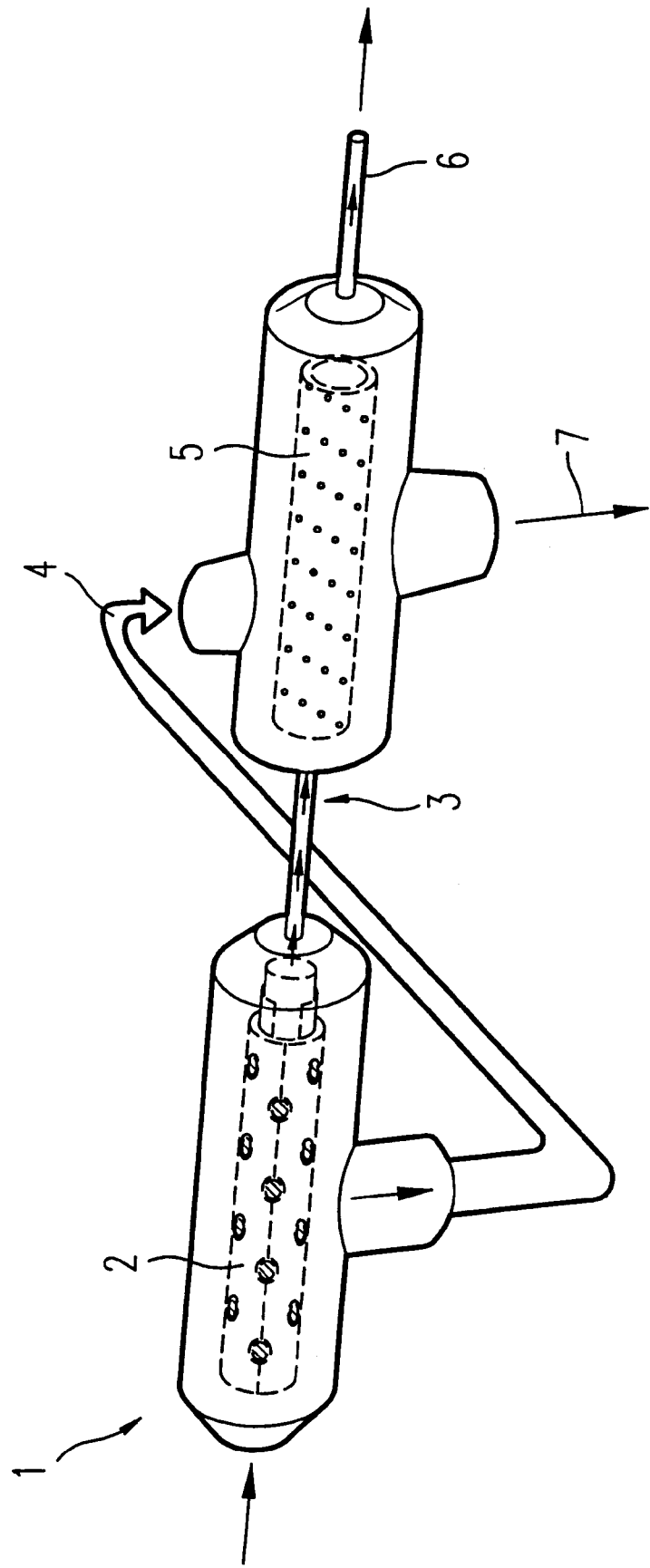
FIG. 3 is a schematic of the preferred embodiment of a bioartificial kidney in accordance with the present invention. (1) Arterial blood delivered to lumen of fibers in filter device. (2) Endothelial cell-lined fibers filter blood, from inside lumen to extracapillary space. Filtrate drained. (3) Post-filtered blood delivered to lumen of reabsorbing device. (4) Filtrate delivered to extra-capillary space of reabsorber device. (5) Epithelial cells on outside of fibers reabsorb, add reabsorbate to post-filtered blood within lumen. (6) Blood returned to circulation.

The preferred bioartificial kidney in accordance with the present invention is depicted in FIG. 3. Here, the above described filtration device precedes the above described tubule processing device in series.

Blood containing undesirable impurities such as metabolic waste which flows from the patient's arterial lumen through the filtration device. Ultrafiltrate separated from the blood is directed into the tubule processing device through the perfusion inlet port. Reabsorbent exits through perfusion outlet port, whereupon it is reabsorbed into the vascular veinous flow.

As blood passes through the filtration device, filtrate diffuses through the confluent monolayer and hollow fibers, and collects into the collecting chamber. The filtrate can then be actively reabsorbed by the renal tubule cells located on the surface of the second type of hollow fibers, which are in contact with the filtrate in the chamber. Filtrate which is not reabsorbed exits collecting chamber through urine outlet port.

The filtration device is suitably implanted either subcutaneously or near the peritoneal cavity or near the iliac fossa. The filtrate formed by this device flows directly into the tubule device which is also suitably implanted either subcutaneously, within the peritoneal cavity or within the iliac fossa. This arrangement allows the filtrate to enter the internal compartments of the hollow fiber network which are lined with confluent monolayers of renal tubule cells. The reabsorbate exits into the peritoneal cavity and is reabsorbed into the systemic circulation. After being processed by the tubule device, the final fluid, i.e. urine, is collected by tubing inserted into the ureter to maintain a natural conduit for urine excretion from the individual.

EXAMPLES

Example 1

Endothelial Cell Culture. A permanent human endothelial cell line, designated ECV 304 (Takahashi et al, *In vitro Cell Dev. Biol.* 25:265–274, 1990), was used for the initial studies for ease of use. To extend the gene transfer and tissue engineering constructs, endothelial cells in primary culture from rabbit vasculature, was also developed.

ECV-304 Cell Isolation and Culture

Isolation: ECV-304 (Human Endothelial, transformed) permanent cell line was obtained from American Type Culture Collection (Rockville, M.D.). Culture Conditions: ECV-304 cultures were maintained on tissue culture plates in a humidified, 37°, 5% $CO_2$ incubator, and grown in media M 199 supplemented with 10% heat inactivated fetal calf serum plus 0.1% fungi-bact, with media changed twice a week. Cells were subcultured at a ratio of 1:6 by using a solution of 1° endothelial cells 0.25% trypsin, 1 mM EDTA.

Mesangial Cell Isolation and Culture

Isolation: Mesangial cells were isolated by differential sieving (Krackower et al, *Arch. Pathol.* 58:401–432, 1984). The glomerular size and thus the mesh sizes used for isolation are species dependent (Holdsworth et al, Nephron 22:454–459, 1978). For rabbit glomerular cell isolation, kidneys were removed from anesthetized animals and placed in ice cold PBS using sterile technique. While keeping the kidneys cold, they were decapsulated, the cortex removed and minced. Tissue types were separated by forcing the minced tissue through a 150 micron sieve, washing the tissue with a high volume of PBS through a second 150 micron sieve, and finally catching the glomeruli on the top of a 63 micron sieve. Culture Conditions: Isolated glomeruli were plated and outgrowths maintained on tissue culture plates in a humidified, 37°, 5% $CO_2$ incubator, and grown in RPMI supplemented with 20% heat inactivated fetal calf serum and 0.1% fungi-bact, with media changes two to three times a week. Subculture of rabbit mesangial cells was accomplished by using a solution of 0.05% trypsin, 0.53mM EDTA and passing at a ratio of 1:2 to 1:3. Utilizing the above techniques, a stock of mesangial cells were grown and frozen for future use. There is adequate supply of these cells to complete any necessary studies.

Endothelial Cell Culture

Endothelial cell culture was adapted from well-established methodology (Mi et al, *Surgery* 114:464–470, 1993; McGuire et al, *Lab Invest.* 57(1):94–105, 1987). Twenty-four culture plate wells layered with Matrigel were used. Two cm length segments from the saphenous vein of a sheep were obtained from the donor animal and were rinsed three times in PBS containing 50 units/ml of heparin. The vessel was cleaned carefully with removal of periadventitial fat and connective tissue. The vessel was then cut into rings of less than 2 mm thickness. The tissue rings were then placed in the base of the wells on MATRIGEL and covered with just enough media to keep moist. Media that was used is RPMI-1640, 10% fetal calf serum, and 50 µg/ml of endothelial cell growth supplement (ECGS) with appropriate penicillin/streptomycin additions. Endothelial cells grow as a monolayer on the MATRIGEL extending from the vessel ring explant. After four to eight days the explant was removed and the endothelial cells were allowed to reach confluence. Once confluency was achieved, endothelial cells for passage were collected by treatment with 2% Dispase in calcium-magnesium free HBSS.

Vascular Smooth Muscle Cell (VSMC) Isolation and Culture

Isolation: VSMC were cultured from explants of sheep saphenous vein (Mii et al, 1993). The vessels were procured either from a local slaughter house for allogeneic studies or donor sheep for autologous studies. The saphenous vein was placed in ice cold PBS. Fat and connective tissue were gently scraped off using tweezers and scissors to minimize stretching. The remaining tissue was then be minced, suspended in growth media and plated into tissue culture dishes. VSMC identity was verified by staining with gamma action antibody and microscopic observation of typical "hill and valley" formations. Culture Conditions: Explant cultures were maintained in a humidified, 37°, 5% $CO_2$ incubator, and grown in DMEM supplemented with 10% heat inactivated fetal calf serum plus 0.1% fungi-bact.

Example 2

Gene transfer of hirudin into endothelial cells. A full length cDNA encoding for the hirudin variant HV-2 (Johnson et al, Seminars in Thrombosis 15:302–315, 1989) has been constructed utilizing dual asymmetric polymerase chain reaction (PCR) in which four adjacent oligonucleotides of 76 to 89 bases in length having short overlaps of 14 bases were used as primers in a PCR mixture (Sander et al, Biotechniques 12:14–16, 1992). In constructing this cDNA, a signal sequence for von Willebrand factor (vWF) was-incorporated in frame 5' to the hirudin gene to ensure secretion of hirudin from transduced cells; protein coding sequences were selected based upon optimal codon usage in rabbit and human genetic sequence data (Wada et al, Nucl. Acids Res. 19:1981–1986, 1991), and appropriate restriction enzyme cut sites 5' and 3' to the cDNA encoding the vWF signal peptide and hirudin HV-2 for ease of transfer into the retroviral vector. The sequence of the constructed cDNA was confirmed to be the desired sequence by bidirectional cloning utilizing the dideoxy chain termination reaction. Utilizing the retroviral vector MFG derived from the Moloney murine leukemia tumor virus (Dranoff et al, Proc. Natl. Acad Sci. 90:3539–3543, 1993) and the packaging cell line (Danos et al, Proc. Natl. Acad. Sci. 85:6460–6464, 1988), ψ-crip, an amphotropic, replication defective, recombinant retrovirus has been constructed containing the required gene sequence.

The retroviral vector pMFG-Hir constructed from PMFG was cotransfected with PSV2-Neo into the amphotropic retroviral packaging cell line, ψ-crip. Resulting clones were isolated by culturing in selective media containing the aminoglycoside, G418. The culture media from various clones were used to infect NIH 3T3 cells. Ninety six clones were screened for production of high titer amphotrophic recombinant retrovirus using Southern blot analysis with a radiolabelled hirudin cDNA probe. Of the 96 clones, 31 were positive with 17 being strongly positive. Twelve of the strongly positive viral producing clones were seeded into 10 cm plates ($5 \times 10^5$ cells per plate) in DMEM containing 10% fetal calf. serum and penicillin/streptomycin. Twenty-four hours after seeding, the media was changed, and after an additional 24 hours the virus containing supernatant was harvested and filtered through a 0.45 µm filter. Rabbit aortic endothelial cells were prepared after growth in primary culture and 2 or 3 serial passages. Under subconfluent conditions, endothelial cells were exposed to undiluted stock of recombinant retrovirus for 24 hours in the presence of Polybrene (8 µg/ml). After transduction the culture medium was then removed and replaced with culture medium. Cells were then grown to confluence and used for various assays.

To test for hirudin protein secretion from transduced endothelial cells, several assays can be used Carey, Ann. Rev. Physiol. 53:161, 19919). For concentrations of hirudin above 5.0 µg/ml, the prothrombin time or activated partial thromboplastin time are effective assays for functional activity of hirudin. For more sensitive and precise assessment of hirudin activity, measurement of catalytic activity of this protein with amidolytic methods (Carey, 1991) has been used to quantitate levels below 5.0 µg/ml. Recently developed ELISA kit assay for hirudin can also be used for sensitive assessment of secreted levels. Recombinant hirudin for positive control assays has been obtained from Dr. R. B. Wallis (Ciba Pharmaceuticals, England). Cell culture supernatants were obtained from rabbit endothelial cells exposed to recombinant retrovirus obtained from two separate clones and were found to contain 377 and 704 ng/ml of hirudin activity secreted over 24 hours. The other clones did not promote measurable protein secretion.

Example 3

Figure 4:
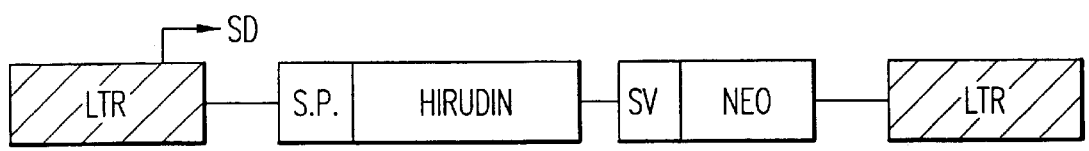
FIG. 4. Basic retroviral vector construct containing the hirudin gene. The vector is a derivative of MoMLV. The signal peptide used for endothelial secretion is plasmin activator inhibitor (PAI)1; LTR, long terminal repeat; SD, splicing donor site; SV, SV-40 promoter.
Figure 5A:
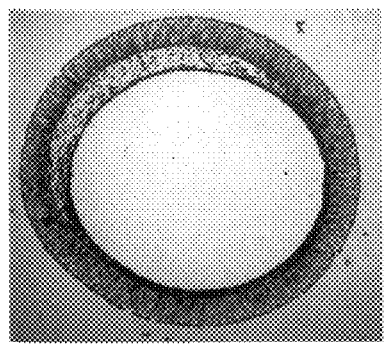
FIG. 5. Light micrographs of a hollow fiber seeded with mesangial cells grown as a supporting mesenchymal layer. Panel a: low power cross section of a tissue engineered hollow fiber with the mesangial support layer with an overlaying confluent monolayer of endothelial cells. Upon sectioning, the upper left area of the cell layer separated from the surface of the synthetic polymer. Panel b: Higher power of the lower edge of (a) demonstrating the smooth endothelial monolayer overlaying the mesenchymal cell layer. Panel c: Similar to (b), except displaying the loosened area of the upper portion of (a). Panel d: High power of a hollow fiber constructed with only mesangial cells and without endothelial cells. As seen, compared to panels (b) and (c), the smooth covering of endothelial cells is not observed.
Figure 5B:
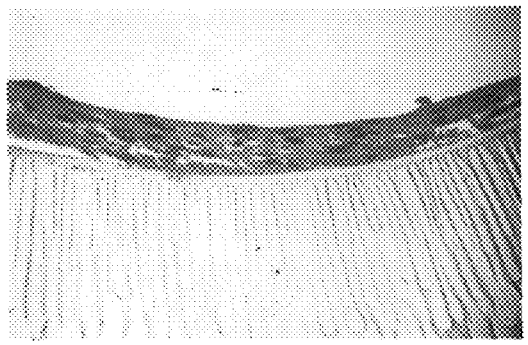
Figure 5C:
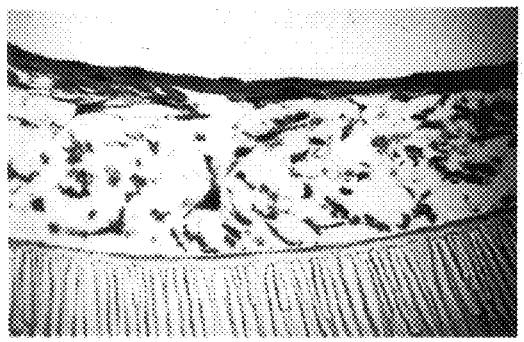
Figure 5D:
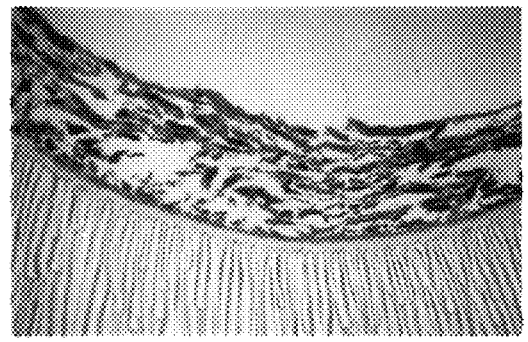
Figure 8:
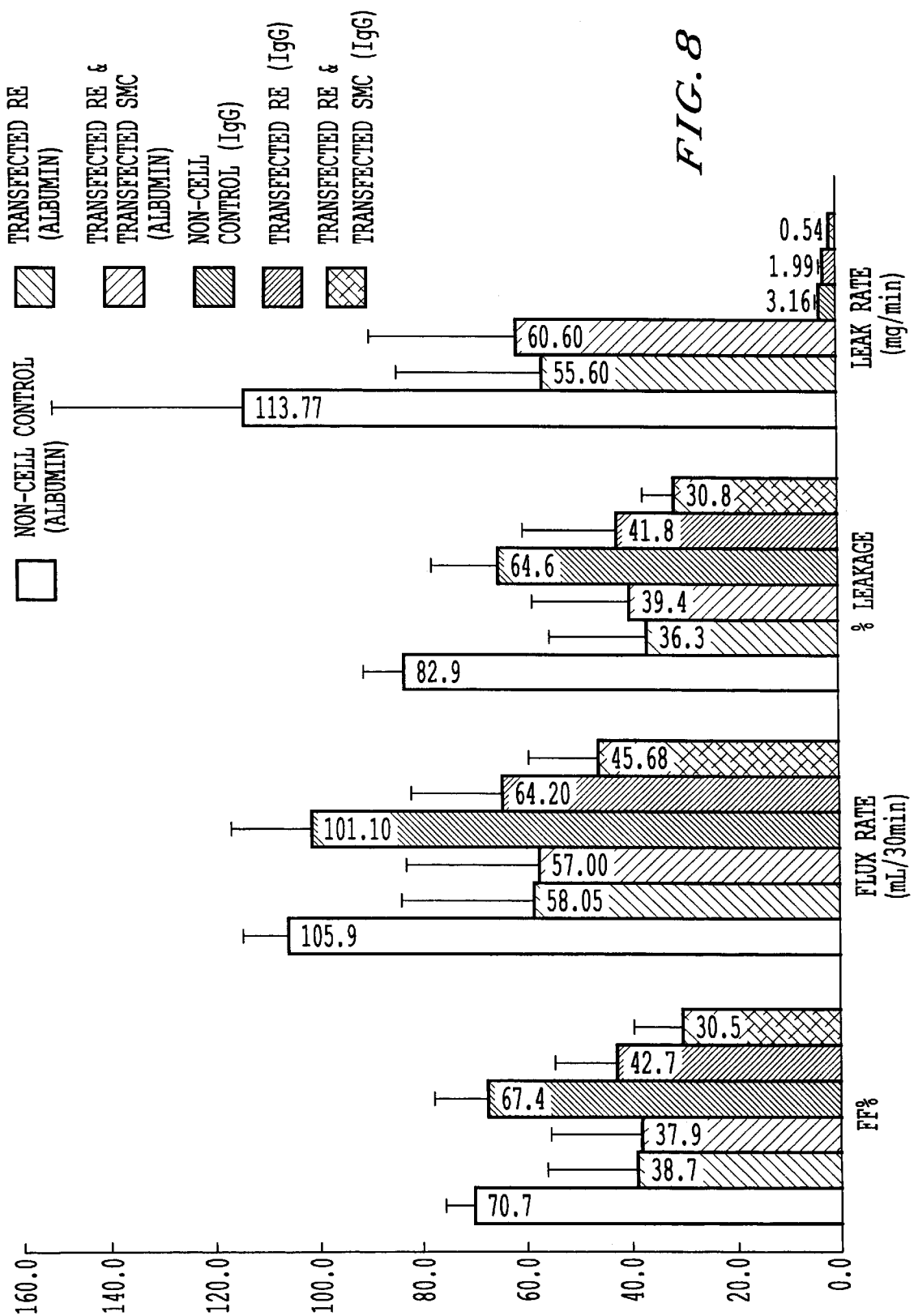
FIG. 8 is a bar graph illustrating filtration fraction (FF)%, flux rate (ml/30 min), % leakage and leak rate (mg/min) for albumin vs. IgG.
Figure 11:
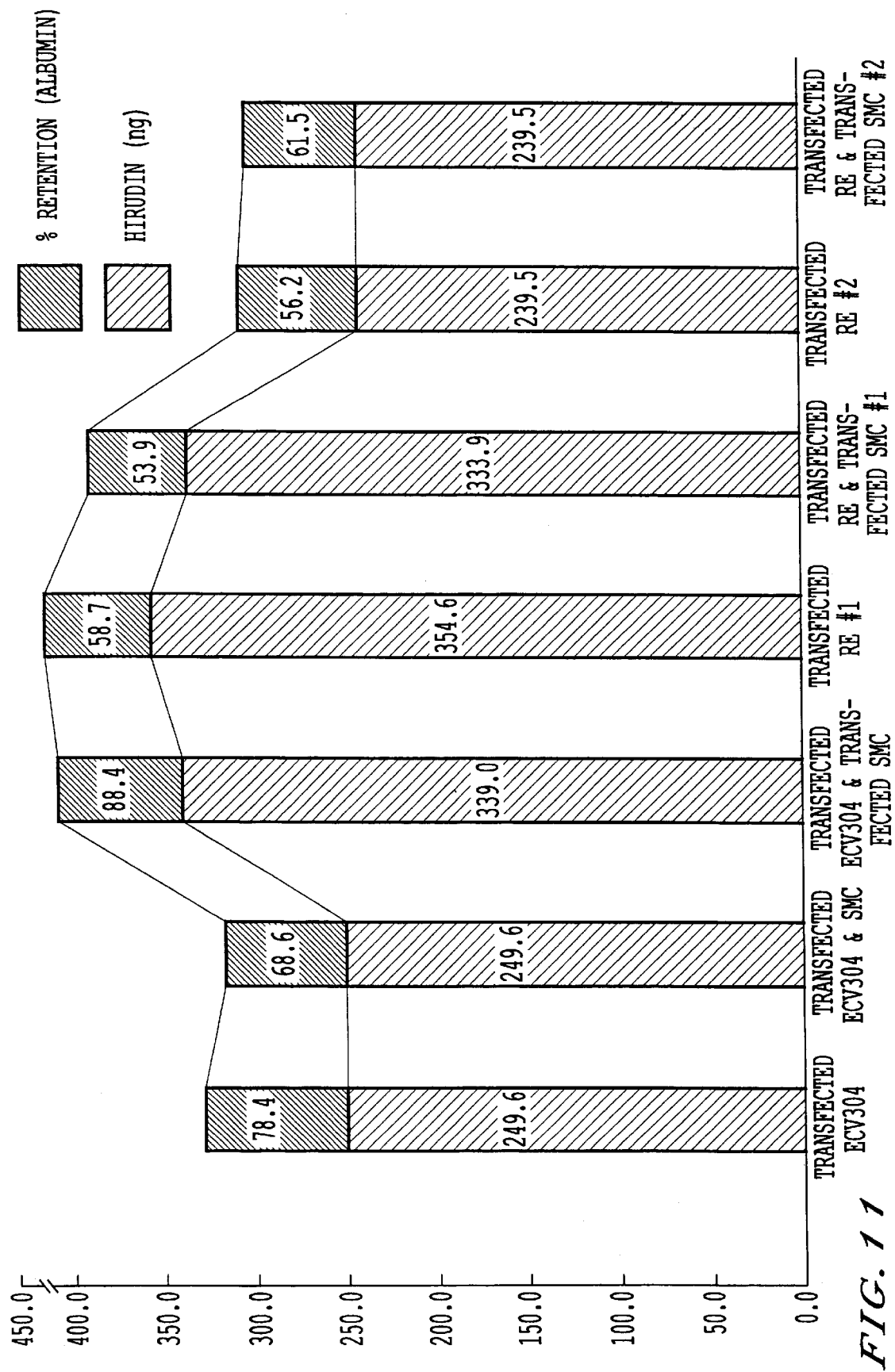
FIG. 11 is a bar graph showing % retention and hirudin production of various transfected cells.

Improved Retroviral Gene Transfer for Hirudin Production. To improve hirudin protein production and secretion by endothelial cells, a different retroviral construct was developed, as detailed in FIG. 4. In this regard, introduction of a drug-selectable marker that is coexpressed with the hirudin gene was planned. Previous strategies have been employed for the coexpression of drug-selectable genes with a second nonselectable gene with the utilization of independent promoters, such as a retroviral LTR and another promoter (Emerman et al, Cell 39:459–467, 1984). With this approach, a replication-defective retroviral vector was constructed capable of efficient constitutive expression of the hirudin gene in mammalian cells by using the LTR promoter. A selectable neomycin (neo) gene, conferring G418 resistance, is under the control of the SV40 promoter. The optimal codon usage in human genetic sequence data was selected to design the hirudin cDNA sequence. A signal sequence for plasminogen activator inhibitor (PA-I) was incorporated in frame 5' to the hirudin gene to ensure secretion of hirudin from transduced endothelial cells. A full length cDNA encoding for hirudin was constructed utilizing dual asymmetric polymerase chain reaction (PCR) in which four adjacent oligonucleotides were used as primers in a PCR mixture. The hirudin cDNA was then inserted into the Bam HI and Sal I sites of the retroviral vector. Infectious, helper-free replication-defective retroviruses were then obtained by direct transfection of the recombinant retroviral vector into amphotropic ψ crip packaging cells with the calcium phosphate precipitation method, and cells were selected for G418 resistance (1 mg/ml). Resistant colonies were isolated and screened for recombinant retrovirus production. ECV 304 cells were infected overnight with the virus containing supernatant in the presence of 8 μg of Polybrene per ml and selected in the medium containing 1 mg of G418 per ml. Resistant colonies were selected and expanded into large cultures. Hirudin secreted into the cell medium was quantitated by a standardized ELISA (American Diagnostics, Inc.). These cells were demonstrated to produce 0.95 ng/$10^6$ cells/24 h.

Example 4

Initial Prototype of Bioartificial Hemofilter.

With the successful transfection of endothelial cells with the hirudin vector and successful secretion of the protein into the cell supernatant, the initial prototype was constructed. A commercially available bioreactor for endothelial cell expansion as a lining monolayer was obtained from CELLCO, Inc. (Baltimore, Md.) The CELLCO Unit is comprised of 50 polypropylene hollow fibers. Each fiber has an inner diameter of 330 μm and an outer diameter of 630 μm. The fibers are microporous with pore size of approximately 0.5 μm with a high filtration rate of 29 ml/min $M^2$·mm Hg. To improve attachment and growth of endothelial cells along the inner surface of the hollow fibers, the fibers were coated with Pronectin-F. Pronectin-F is a recombinant protein containing multiple copies of the RGD cell attachment ligand of human fibronectin interspersed between repeated structural peptide segments derived from spider silk, thereby providing a nondegradable highly stable substrate for cell attachment.

To construct the BHF, ECV304 cells were seeded into a CELLCO polypropylene fiber unit at a concentration of $1.2 \times 10^7$ cells/mL. The cell suspension was allowed to incubate at 37° C. for 90 minutes. After this incubation, the bioreactor was rotated 90° and another seeding of cells was performed. This process was repeated two more times to complete a 360° seeding of the hollow fibers. The final cell suspension was flushed from the fibers after the final seeding. Extracapillary space (ECS) perfusion with culture media was started 24 hours later. Four days after cell seeding, the bioreactor was perfused intraluminally with M199 media containing 10% FCS at a rate of 500 μL/min. The lumen perfusion rate was increased every 24 hours until 5 mL/min was achieved, to adapt the cells to incremental shear stress.

After 5–7 days of adaptation of the cells to sheer stress, the unit was tested for filtration rate and albumin leak rate and compared to a non-cell seeded unit. The experimental design was the addition of albumin to the perfusion M199 culture media at a concentration of 2.5 gm/dl. The flow rate was 5 ml/min. The collection time period was 10 minutes with a pre-lumen hydraulic pressure of 25 mm of Hg and a post-lumen hydraulic pressure of 10 mm of Hg. As summarized in Table 1, under these experimental conditions (n=3), the non-cell unit had a filtration rate of 3.88 ml/mon, or a filtration fraction of 70.7%. After endothelial cells were seeded and grown as a monolayer, filtration rate fell to 2.20 ml/min with a filtration fraction of 45.3%. Of key importance, the albumin leak rate under these conditions in the non-cell unit was 109.3 mg/min or 82.7% of the perfused albumin, but after endothelial cell seeding and growth, the albumin leak rate significantly declined to 5.8 mg/min or a percent albumin leak rate of 2.6%. Thus, as expected, there was significant diminution in the filtration rate but highly improved pernselectivity characteristics of the bioartificial hemofilter (BIM to reduce the albumin leakage to a small percentage of that which was presented to the BHF.)

TABLE I

|  | Filtration Rate (ml/min) | Filtration Fraction (%) | Albumin leak Rate (mg/min) | Percentage Albumin Leak (%) |
| --- | --- | --- | --- | --- |
| Non-Cell Unit | 3.88 ± 094 | 70.7 ± 5.7 | 109 ± 3.2 | 82.7 ± 7.6 |
| Endothelial Cell Unit | 2.20 ± 0.52 | 45.3 ± 8.5 | 5.0 ± 1.0 | 2.6 ± 0.7 |

In addition, the hirudin level was also measured in the circulating luminal perfusate and was found to be 3.95 ng/unit/24 hours, demonstrating successful transfection and protein hirudin secretion in the BHF. Of note, the amount of hirudin produced by these cells was calculated to be 0.02 ng/$10^6$ cells/24 hours in comparison to the production and secretion rate of 0.95 ng/$10^6$ cells/24 hours when the same endothelial cells were grown on a 10 cm culture plate prior to seeding. Thus, the predicted maximal amount of hirudin production in the BHF should have been 161 ng/unit/24 hours, so that only 2.5% of predicted hirudin production was observed when these cells were grown as a confluent monolayer along the hollow fibers. Of importance, this rate of hirudin production is several orders of magnitude higher than has been achieved in prior reports (Rade et al, *Nat. Med.* 2:293–298, 1996). This decline may be due to differences of protein production and secretion due to the extracellular matrix that the cells are grown. However, the improved permselectivity and leakage to albumin demonstrates that a microporous synthetic hollow fiber can be converted to a highly selective permselective barrier to albumin translocation across an endothelial cell layer when properly constructed.

Example 5

Improved Prototypes for Bioartificial Hemofilter

With the initial results, detailed above, that high filtration rates can be maintained with a confluent endothelial monolayer simultaneously to excellent permselectivity characteristics to albumin, further refinements to improve durability of this device were then approached. With the objective of attaining in a BHF a filtration rate of 2–4 ml/min, it was acknowledged that additional cellular components could be added to the lining layer of endothelium to improve the durability and hirudin production rates without significant sacrifice of fluid flux to achieve this desired filtration rate. This objective of attaining a 2–4 ml/min filtration rate for an-implantable device provides a filtration rate of 2–5 liters/24 hrs, a fluid volume that can be maintained in an ESRD patient without risk to severe volume depletion and tolerable frequencies for urinary bladder emptying.

Mesenchymal support cells assist endothelial cell differentiation and performance characteristics (Morel, *FASEB J.* 7:1031–1038, 1993). For middle size vessels, both arterial and venous, smooth muscle cells are a component for vessel tone and maintenance (Sato et al, *J. Cell Biol.* 111:757–763, 1990). At the capillary level, the pericyte, which is a smooth muscle cell variant, also provides components for endothelial cell maintenance and capillary functional performance (Morel, 1993). For the glomerular capillary tuft, a further refined smooth muscle cell variant, the mesangial cell, maintains capillary structure and function within the complex glomerular capillary architecture (Scheinman et al, *Lab. Invest.* 34:150–158, 1976). In this regard, an approach was initiated to provide this mesenchymal support structure to further refine the initial tissue engineered device to provide not only supporting cells for the endothelial monolayer but also another source for gene transfer of hirudin for protein production and secretion into the surrounding microenvironment. Accordingly, mesangial cells were grown in tissue culture and seeded into single hollow fibers and followed within 1–7 days by endothelial cell seeding. As demonstrated in FIG. 5, after several days growth the histologic evaluation of fiber demonstrated concurrent growth of both cell types along the inner aspect of the hollow fiber with a smooth confluent endothelial monolayer being at the interface between the mesenchymal cell layer and the perfused lumen.

These single fibers were then evaluated with pressure and flows which simulate in vivo conditions, At 25 $\mu$l/min of media flow at hydraulic pressures of 50 and 25 mm Hg, the single fibers (2 cm in length) filtered at a rate of 2.8 and 1.2 $\mu$l/min, respectively. This corresponds to a filtration rate with comparable scaled up flow rates of approximately 40 ml/M$^2$ and 17 ml/M$^2$ values well within the desired limits of 2–4 ml/min. Therefore, the addition of this mesangial support layer retarded filtration rates but not below the desired levels for the implantable device.

Example 6

Identification of optimal extracellular matrix protein for the bioartificial hemofilter.

ECV304 endothelial cells and vascular smooth muscle cells are utilized in the device after coating the inner surface of the hollow fibers with several different extracellular matrix (ECM) proteins. The extracellular proteins which aid in the attachment and expansion of the vascular smooth muscle cells include pronectin F, fibronectin, a well described matrix molecule important for mesenchymal cell attachment and growth, and collagen type I, a key collagen type used by mesodermal cells for attachment and growth. The intraluminal fiber surface is pre-coated with these proteins, at which time the vascular smooth muscle cells are seeded into the device with the 90° rotational seeding to complete a 360° process. After growth of the smooth muscle cells over 5–7 days, the ECV304-cells are seeded in a similar 360° rotational process. The cocultures are grown over the next 5–7 days and then tested under physiologic flow and pressure conditions to assess filtration and permselective characteristics to albumin. From these experiments the best consistency of performance with various ECM molecules of this tissue engineered bioartificial hemofilter are assessed based upon functional characteristics of filtration rate and albumin permiselectivity. The amount of hirudin production is also assayed in these devices which have been constructed with cells that have been previously transduced with the recombinant retrovirus containing the hirudin gene. The amount of hirudin production is also a key assessment of the effect of the matrix material on gene expression and may be an important element in the selection of the ECM compound.

Example 7

Extra corporeal ex vivo performance testing of the bioartificial hemofilter in animals short-term:

Sheep are used to test the performance of the bioartificial hemofilter in an Extra corporeal circuit utilizing allogeneic endothelial and vascular smooth muscle cells from a donor animal. Sheep are anesthetized and two catheters are placed in the animal, the first in the carotid artery for arterial access and the second in the internal jugular vein similar to the approach used for arteriovenous hemofiltration. The Extra corporeal circuit uses standard arterial and venous blood tubing and is connected to the bioartificial hemofilter similar to standard clinical connections utilizing a synthetic hemofilter for therapy of acute renal failure. The bioartificial hemofilter is primed with normal saline containing heparin and, prior to connection, the animal receives an initial heparin bolus of 1000 IU. A continuous heparin infusion is administered through a pre-hemofilter access port continuously running at an hourly infusion rate between 200–500 IU per hour to prevent clotting in the Extra corporeal circuit. The heparin dose is adjusted day to day based upon the activated clotting times obtained from the animal. If replacement fluid is required, it is infused in the animal to maintain a euvolemic condition with normal saline. Because allogeneic cells and not autologous cells may be used, the device is used for only 4–5 days to test for short-term durability and functional testing prior to immunologic rejection. On a daily basis, ultrafiltrate is collected to assess filtration rates and the permiselective characteristics of the bioartificial hemofilter while it is in place within the Extra corporeal circuit ex vivo. The ultrafiltrate is also assessed for hirudin secretion levels to determine the efficacy of hirudin production in the device as well. The achievement of performance characteristics which maintain an ultrafiltration rate between 2–4 ml/min and permiselectivity to albumin to minimize albumin leakage into the ultrafiltrate of less than 2 grams per day is preferred. Furthermore, hirudin production rates approaching microgram quantities with the incremental cell number is also preferred. Venous blood is collected daily for activated clotting times as well as measurement of circulating systemic hirudin levels to assess whether hirudin production with the device is having systemic effects.

Example 8

Long Term Studies in Non-Uremic Animals

Sheep are used to assess the long-term function and durability of the BHF. Sheep are prepared for implantation of the bioartificial hemofilter and appropriately anticoagulated acutely with heparin for the first several days after the operation until the coumadin dose can be adjusted to elevate the prothrombin time to twice normal. The animal is anesthetized.

The sheep are fasted overnight prior to surgery. Anesthesia is induced via sodium pentathol I.V. (20 mg/kg) and maintained on 1.5% isoflorene gas. For the Extra corporeal ex vivo animals an arterial venous shunt is created by placing silastic tubing (5 mm I.D., 8 mm O.D.) in the carotid artery. This tubing is connected to the entrance port of the bioartificial hemofilter, the exit port tubing is then placed in the jugular vein in order to complete the AV circuit. Blood flow is monitored utilizing a blood flow meter at both the entrance and the exit ports of the bioartiflcial hemofilter. Systemic venous blood is drawn from the cephalic vein via a 21 gauge butterfly. Large animal metabolic cages are used for 24 hour urine collections. For the long-term function and durability studies sheep are first utilized for autologous saphenous vein endothelial and smooth muscle cell procurement. After induction of anesthesia the hind leg is shaved and prepped. An incision lateral to the saphenous vein is made, all vascular branches are isolated and ligated, the vein is excised and the area observed for bleeding. The incision is closed and the sheep allowed to recover for 21 days (cells are grown and prepared over this time period). For device implant, anesthesia is induced and an incision is made in the iliac fossa. The common iliac artery and vein is anastamosed to EPTFE graft material which is connected to the entrance and exit port of the bioartificial hemofilter. The ultrafiltrate port tubing (1–3 mm O.D.) is placed in the ureter and secured by suture. The device is anchored to the abdominal wall by suture. For the uremic model, a 1 and 5/6 nephrectomy is performed. A midline incision is made. Renal arteries, veins and ureter is isolated and ligated. Kidney and partial kidney are removed. Bleeding are stopped by applying pressure with gel foam. After nephrectomy the device is implanted as described above. After surgical closure, sheep are monitored until awake and standing. Sheep are housed in 4×8 pens (2 per cage). There are 10–15 air exchanges each hour. Sheep are fed Purina sheep chow and alfalfa hay.

As described above, activated clotting times and prothrombin times are monitored on a daily basis until a long term coumadin dose to elevate prothrombin times to twice normal levels is achieved. Daily urines are collected on a timed basis for the first two weeks of this study to measure the rate of hirudin excretion in the urine as an indirect measure of functional durability and compared to the functional performance of the hemofilter based upon base-line hirudin production rates ex vivo prior to implantation. Hirudin production should be directly correlative to the cell viability within the device and non-clotting of the device. This measurement is used as a surrogate marker of functional performance. The urine is also assessed for urinary albumin excretion and compared to base-line urinary albumin excretion prior to surgery. After the first two weeks, weekly 24 hour urine collections are made to measure hirudin and albumin excretion rates for assessment of the functional performance and durability of the implanted device. Sheep are euthanized and the device removed for histological analysis.

Example 9
In Vivo Performance of Bioartificial Hemofilter in Uremic Animals

Sheep are made mildly uremic by performing 1 and 5/6 nephrectomies. The pelvic fossa will be approached through a ventral incision similar to above and a single bioartificial hemofilter connected through an arteriovenous and urethral connections. The animals are followed in a similar manner as detailed above with daily urinary albumin and hirudin levels obtained for the first two weeks and then weekly functional measurements obtained thereafter. Simultaneously, measurement of renal function with serum BUN and creatinine levels are assessed. Once again, urinary hirudin and albumin excretion rates are utilized as indirect measures of functional viability and performance of the implanted device. Urine outputs are measured intermittently, especially in the first two weeks, to ensure that the filtration rate is not excessive, to avoid volume depletion. If there is an excessive ultrafiltration rate, saline infusion may be necessary to maintain euvolemia in the animals. Sheep are euthanized and the device will be removed for histological analysis.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A bioartificial filtration device suitable for filtering blood comprising a bundle of semipermeable hollow fibers in a chamber defined by a housing having a perfusion inlet port, a perfusion outlet port and a blood filtrate outlet port, wherein said semipermeable hollow fibers are coated internally and/or externally with a first population of cells selected from the group consisting of nonimmortalized endothelial cells, epithelial cells, or a mixture thereof, and a second population of cells selected from the group consisting of pericytes, vascular smooth muscle cells, mesangial cells or a mixture thereof, wherein opposite ends of said bundle of semipermeable hollow fibers are connected to the perfusion inlet and outlet ports.

2. The bioartificial filtration device of claim 1, wherein the first population of cells consists of epithelial cells, wherein said epithelial cells are renal tubule cells.

3. The bioartificial filtration device of claim 2, wherein said second population of cells consists of pericytes.

4. The bioartificial filtration device of claim 1, wherein said second population of cells consists of mesangial cells.

5. The bioartificial filtration device of claim 1, wherein said second population of cells consists of pericytes.

6. The bioartificial filtration device of claim 1, wherein said first population of cells and second population of cells are in at least a ratio of 1:1, and wherein said first population of cells consists of nonimmortalized endothelial cells.

7. The bioartificial filtration device of claim 1, wherein said first population of cells and said second population of cells are coated on said semipermeable hollow fibers as a mixed population of cells.

8. The bioartificial filtration device of claim 1, wherein said first population of cells and said second population of cells are coated on said semipermeable hollow fibers as distinct layers of populations of cells.

9. The bioartificial filtration device of claim 8, wherein said second population of cells consists of vascular smooth muscle cells.

10. The bioartificial filtration device of claim 1, wherein said first population of cells consists of nonimmortalized endothelial cells.

11. The bioartificial filtration device of claim 10, wherein said second population of cells consists of vascular smooth muscle cells.

12. The bioartificial filtration device of claim 1, wherein said first population of cells consists of epithelial cells.

13. The bioartificial filtration device of claim 1, wherein said first population of cells consists of a mixture of nonimmortalized endothelial cells and epithelial cells.

14. The bioartificial filtration device of claim 1, wherein said second population of cells consists of vascular smooth muscle cells.

* * * * *

UNITED STATES PATENT AND TRADEMARK OFFICE
CERTIFICATE OF CORRECTION

PATENT NO.   : 6,150,164
DATED        : NOVEMBER 21, 2000
INVENTOR(S)  : H. David HUMES It is certified that error appears in the above-identified patent and that said Letters Patent is hereby corrected as shown below:

Column 8, line 45, "106" should read --106,--.

Column 8, lines 55-56, "immunoprotection" should read --Immunoprotection--.

Column 11, line 24, after "then" delete "be".

Column 13, line 65, "pernselectivity" should read --permselectivity--.

Signed and Sealed this

Fifth Day of June, 2001

*Attest:*

*Attesting Officer*

NICHOLAS P. GODICI

*Acting Director of the United States Patent and Trademark Office*